United States Patent
Gambale et al.

(10) Patent No.: US 6,315,778 B1
(45) Date of Patent: Nov. 13, 2001

(54) APPARATUS FOR CREATING A CONTINUOUS ANNULAR LESION

(75) Inventors: Richard Gambale, Tyngsboro, MA (US); Gary S. Falwell, Manchester, NH (US); Donald Patterson, North Chelmsford, MA (US); Michel Haissaguerre, Talence (FR); Sean Forde, Watertown, MA (US)

(73) Assignee: C. R. Bard, Inc., Murray Hill, NJ (US)

(*) Notice: Subject to any disclaimer, the term of this patent is extended or adjusted under 35 U.S.C. 154(b) by 0 days.

(21) Appl. No.: 09/396,502

(22) Filed: Sep. 10, 1999

(51) Int. Cl.⁷ .................................................. A61B 18/18
(52) U.S. Cl. ........................ 606/41; 606/46; 606/47; 607/101; 607/122
(58) Field of Search ........................... 606/41, 22, 25, 606/46, 47; 607/101, 102, 150

(56) References Cited

U.S. PATENT DOCUMENTS

| | | | |
|---|---|---|---|
| 3,902,501 | 9/1975 | Citron et al. | 128/418 |
| 3,996,938 | 12/1976 | Clark, III | 128/348 |
| 4,640,298 | 2/1987 | Pless et al. | 128/784 |
| 4,660,571 | 4/1987 | Hess et al. | 128/784 |
| 4,664,120 | 5/1987 | Hess | 128/642 |
| 4,669,488 | 6/1987 | Hess | 128/785 |
| 4,825,871 | 5/1989 | Cansell | 128/419 |
| 4,921,484 | 5/1990 | Hillstead | 604/104 |
| 5,010,894 | 4/1991 | Edhag | 128/785 |
| 5,100,423 | 3/1992 | Fearnot | 606/159 |
| 5,170,802 | 12/1992 | Mehra | 128/784 |
| 5,190,052 | 3/1993 | Schroeppel | 128/786 |
| 5,324,284 | 6/1994 | Imran | 606/15 |
| 5,409,000 | 4/1995 | Imran | 128/642 |
| 5,462,527 | 10/1995 | Stevens-Wright et al. | 604/95 |
| 5,531,779 | 7/1996 | Dahl et al. | 607/119 |
| 5,575,810 | 11/1996 | Swanson et al. | 607/99 |
| 5,611,777 | 3/1997 | Bowden et al. | 604/95 |
| 5,680,860 | 10/1997 | Imran | 128/642 |
| 5,702,438 | 12/1997 | Avitall | 607/122 |
| 5,738,683 | 4/1998 | Osypka | 606/47 |
| 5,782,898 | 7/1998 | Dahl et al. | 607/119 |
| 5,800,494 | * 9/1998 | Campbell et al. | 607/116 |
| 5,820,629 | 10/1998 | Cox | 606/159 |
| 5,829,447 | 11/1998 | Stevens et al. | 128/898 |
| 5,836,947 | 11/1998 | Fleischman et al. | 606/47 |
| 5,860,920 | * 1/1999 | McGee et al. | 600/374 |
| 5,860,974 | 1/1999 | Abele | 606/41 |
| 5,971,983 | * 10/1999 | Lesh | 606/41 |
| 6,012,457 | 1/2000 | Lesh | 128/898 |
| 6,024,740 | 2/2000 | Lesh et al. | 606/34 |

FOREIGN PATENT DOCUMENTS

| | | | | |
|---|---|---|---|---|
| 0771547 A2 | 7/1997 | (EP) | | A61B/17/39 |
| 2 271932A | 5/1994 | (GB) | | A61B/17/38 |
| WO 96/10961 | 4/1996 | (WO) | | A61B/17/39 |
| WO 93/16632 | 9/1993 | (WO) | | A61B/5/04 |
| WO 94/21165 | 9/1994 | (WO) | | A61B/5/04 |
| WO 94/21167 | 9/1994 | (WO) | | A61B/5/04 |
| WO 94/21168 | 9/1994 | (WO) | | A61B/5/04 |
| WO 97/17892 | 5/1997 | (WO) | | A61B/5/04 |
| WO 95/01751 | 1/1995 | (WO) | | A61B/8/12 |
| WO 95/10318 | 4/1995 | (WO) | | A61N/1/05 |
| WO 95/10319 | 4/1995 | (WO) | | A61N/1/05 |

* cited by examiner

*Primary Examiner*—Linda C. M. Dvorak
*Assistant Examiner*—David Ruddy
(74) *Attorney, Agent, or Firm*—Darby & Darby

(57) ABSTRACT

A medical device is disclosed which includes a deformable electrode device. In one illustrative embodiment, the deformable electrode is in the form of a braided member, at least a portion of which is electrically conductive. The braided member is extended over an elongated inner member, such as a guide wire, catheter shaft, or the like. A proximal sheath is slidably extended over the inner member and is connected to the braided, electrically conductive member. The proximal sheath may be advanced distally to deform the braided member so that it defines a distally facing, ablative ring, and is operative to form an annular lesion.

40 Claims, 3 Drawing Sheets

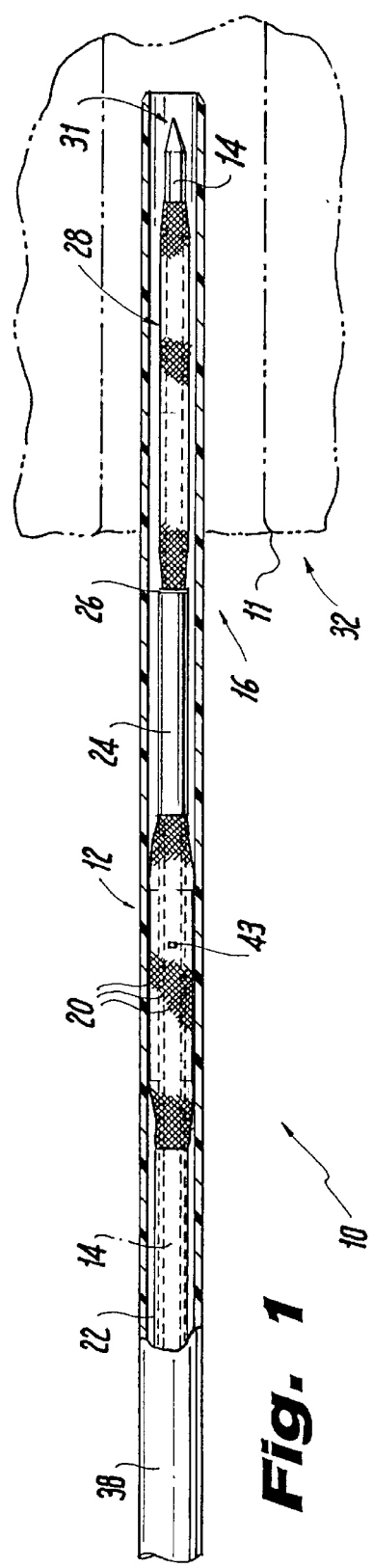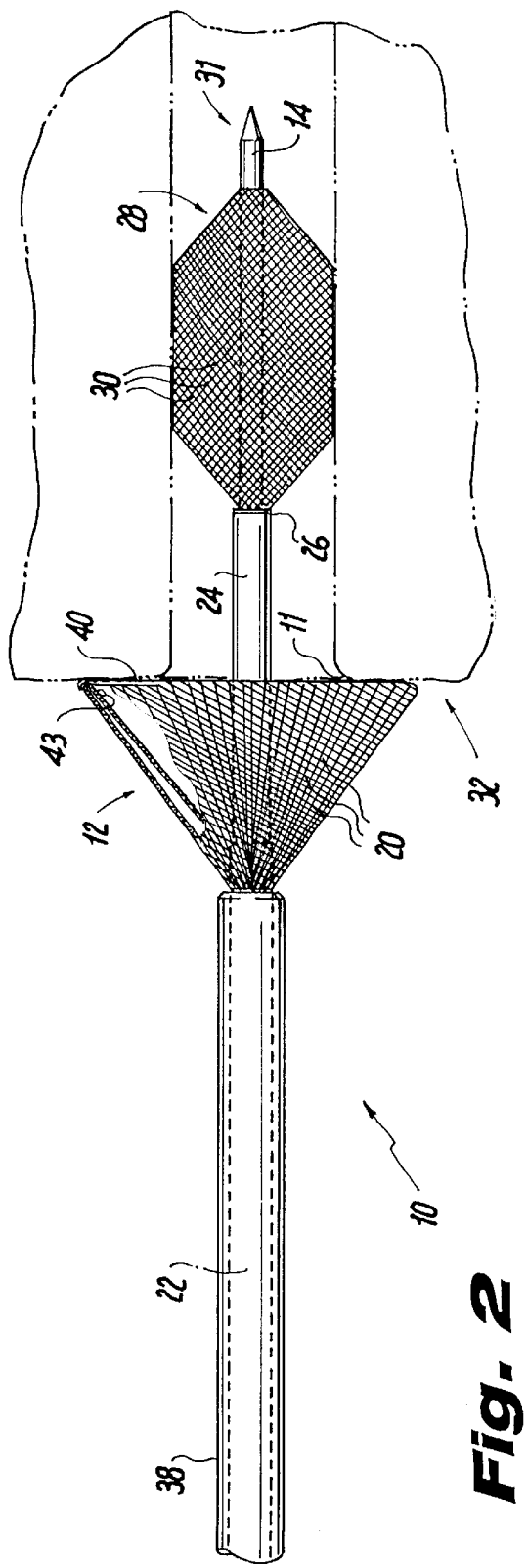

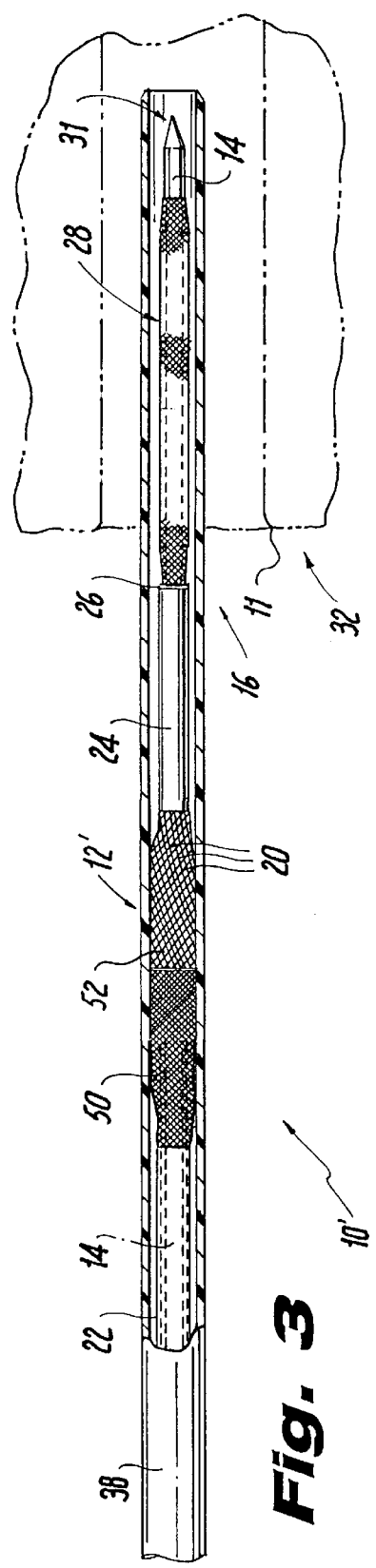
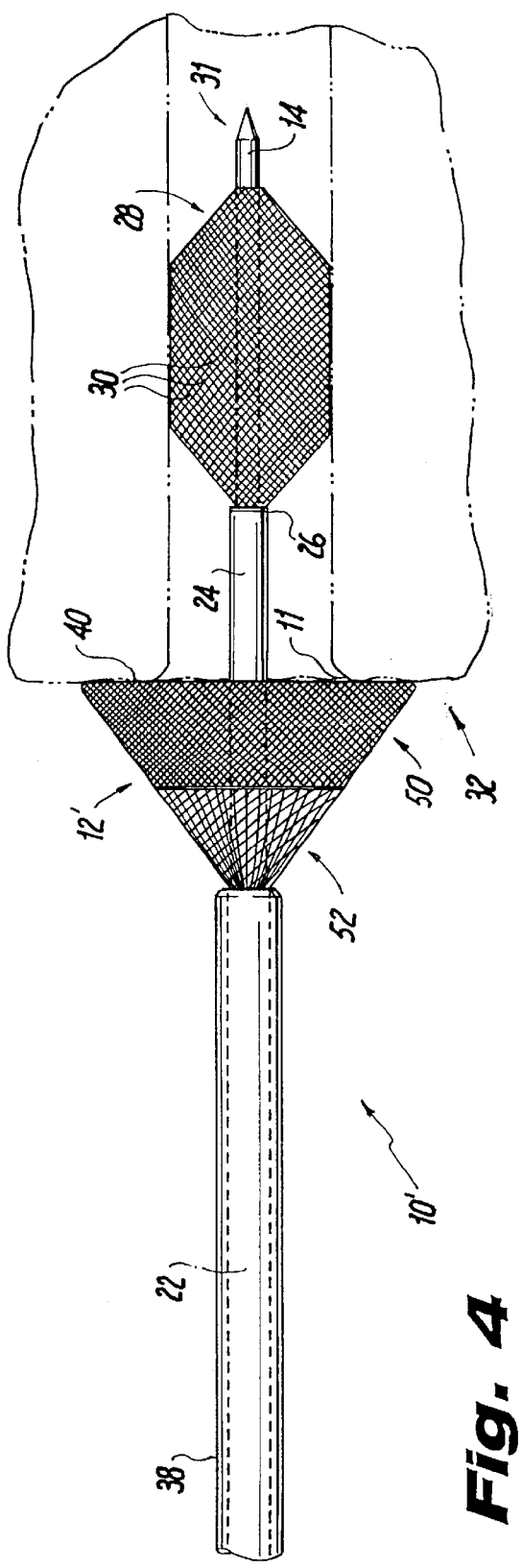

APPARATUS FOR CREATING A CONTINUOUS ANNULAR LESION

FIELD OF THE INVENTION

This invention relates to medical devices for performing ablative procedures and, more particularly, to a medical device which is capable of ablating a continuous ring of tissue in a single step.

BACKGROUND OF THE INVENTION

The human heart is a very complex organ, which relies on both muscle contraction and electrical impulses to properly function. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Non-surgical procedures, for example, management with drugs, are favored in the treatment of cardiac arrhythmias. However, some arrhythmias are not treatable with drugs. For example, drug therapy to combat certain types of cardiac arrhythmias has been found to be successful in only 30 to 50 percent of patients. Because of this low success rate, another conventional remedy is to perform a surgical procedure. According to these procedures, various incisions are made in the heart to block conduction pathways in an effort to abolish the arrhythmia.

Minimally invasive techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways. The regions to be ablated are usually first determined by endocardial mapping techniques. Mapping typically involves percutaneously introducing a catheter having one or more electrodes into the patient, passing the catheter through a blood vessel (e.g. the femoral vein or aorta) and into an endocardial site (e.g., the atrium or ventricle of the heart), and inducing a tachycardia so that a continuous, simultaneous recording can be made with a multichannel recorder at each of several different endocardial positions. When a tachycardia focus is located, as indicated in the electrocardiogram recording, it is marked by means of a fluoroscopic image so that cardiac arrhythmias at the located site can be ablated. An ablation catheter with one or more electrodes can then transmit electrical energy to the tissue adjacent the electrode to create a lesion in the tissue. One or more suitably positioned lesions will typically create a region of necrotic tissue which serves to disable the propagation to the errant impulse caused by the tachycardia focus.

Ablation is carried out by applying energy to the catheter electrodes once the electrodes are in contact with the cardiac tissue. The energy can be, for example, RF, DC, ultrasound, microwave, or laser radiation. When RF energy is delivered between the distal tip of a standard electrode catheter and a backplate, there is a localized RF heating effect. This creates a well-defined, discrete lesion slightly larger than the tip electrode (i.e., the "damage range" for the electrode), and also causes the temperature of the tissue in contact with the electrode to rise.

It has been found that to overcome focal arrhythmias (a form of cardiac arrhythmia), it is often necessary to create a continuous, annular lesion around the ostia (i.e., the openings) of either veins or arteries leading to or from the atria. Conventional techniques include applying multiple point sources around the ostia in an effort to create a continuous lesion. Such a technique is relatively involved, and requires significant skill and attention from the clinician performing the procedure.

Accordingly, it will be apparent that there continues to be a need for a device for performing ablations which facilitates the creation of continuous, annular lesions. In addition, there exists the need for such a device which may pass through relatively narrow passageways to arrive at the site of interest. The instant invention addresses these and other needs.

SUMMARY OF THE INVENTION

According to one aspect of the invention, a deformable electrode structure is extended over a tubular inner member, such as a catheter shaft, guide wire, or the like. The electrode structure is deformable to assume a distally facing, ablative ring, to simultaneously ablate a ring of tissue, and is also collapsible to facilitate manipulation of the device through a patient's vasculature.

In one illustrative embodiment, the electrode structure is in the form of an elongated, braided electrode which is slidably extended over the inner member. An actuating member is also slidably extended over the inner member and is connected to the braided electrode. Advancement of the actuating member distally relative to the inner member causes the braided electrode structure to expand radially outwardly and assume a generally disk shape. Further advancement of the actuating member causes the braided electrode structure to buckle and thereby assume a generally conical shape which defines the distally facing, ablative ring.

In another illustrative embodiment, the invention includes a stabilizing and centering member which is configured for insertion into a patient's vessel (e.g., an artery or vein leading to or from a chamber of interest) and is expandable inside the lumen to center the device relative to the lumen, and to anchor the device in place for reliable deployment of the ablating electrode.

Thus, in one illustrative embodiment, the present invention is directed to a medical device which includes: an inner tubular member; a braided, electrically conductive member slidably extended over the tubular member; first and second sheaths slidably extended over the tubular member and connected to respective ends of the braided conductive member; a stop formed on the inner tubular member at a location distal of the distal-most sheath; wherein the first sheath is advanceable distally over the inner tubular member to force the second sheath against the stop and cause the conductive member to assume a generally conical configuration and define a distally facing ablative ring.

In another illustrative embodiment, the invention is directed to a medical device for ablating a ring of tissue, including: an elongated inner member; a braided, electrically conductive member slidably extended over the tubular member; and means for deforming the braided, electrically conductive member to define a ring of ablative material.

DESCRIPTION OF THE DRAWINGS

Other objects, features and advantages of the invention discussed in the above summary of the invention will be more clearly understood from the following detailed description of preferred embodiments, which are illustrative only, when taken together with the accompanying drawings in which:

FIG. 1 is a side view of a medical device carrying a deformable electrode illustrating one embodiment of the present invention;

FIG. 2 is a side view similar to FIG. 1 and showing the medical device in a deployed position;

FIG. 3 is a side view of another illustrative embodiment of a medical device according to the invention;

FIG. 4 is a side view similar to FIG. 3 and showing the medical device in a deployed position;

DETAILED DESCRIPTION OF THE PREFERRED EMBODIMENTS

Figure 5:
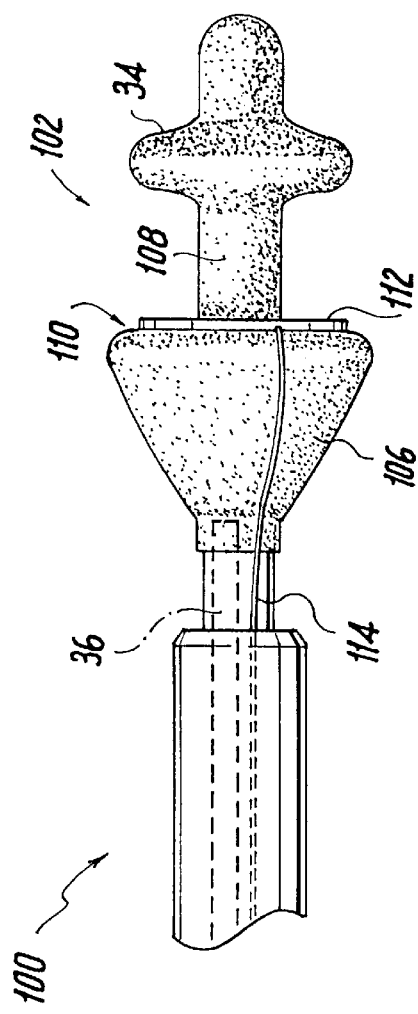
FIG. 5 is a side view of yet another illustrative embodiment of a medical device according to the invention.

Referring now to the drawings, and particularly to FIG. 1, there is shown a medical device 10 according to one illustrative embodiment of the present invention. The medical device 10 is operative to create a continuous, annular lesion around, for example, a patient's ostium 11 (the opening leading to or from an artery or vein within an atrium (shown in phantom in FIGS. 1 through 4)). In one illustrative embodiment, the medical device 10 has a deformable electrode 12 which is slidably extended over an elongated inner member 14 and which is displaceable relative to the inner member in a distal direction along a predetermined travel path, along which the electrode is transformed from a collapsed position (FIG. 1) to a deployed position (FIG. 2). An electrode deployment mechanism, generally designated 16, is provided to selectively transform the electrode between the respective deployed and collapsed positions. The medical device may also include a stabilizer and centering member 28 to securely and reliably position the device 10 relative to the patient's anatomy.

The inner member 14 may be a solid wire or tube, and preferably is electrically conductive. The inner member may comprise a guide wire, catheter shaft, or any other suitable device which is flexible for manipulation through a patient's vasculature to an intended site within the patient. In one illustrative embodiment, the inner member is a steerable catheter which is designed to facilitate manipulation thereof through the patient's vasculature, as is well known in the art.

The deformable electrode 12 is preferably in the form of a braided structure defined by a plurality of interlaced, electrically conductive filaments 20. In the collapsed position shown in FIG. 1, the filaments extend in generally collinear fashion with the inner member 14. The filaments are flexible and capable of being expanded radially outwardly from the inner member and then deformed into the distally facing, deployed configuration as shown in FIG. 2, to define a distally facing, ablative ring 40 that is coaxial with the inner member 14. The filaments are preferably formed of metallic elements having relatively small cross-sectional diameters, such that the filaments can be expanded radially outwardly and then forced to buckle to assume the inverted, generally conical shape, without permanent strain to the individual filaments. The filaments may be round, having a dimension on the order of about 0.002–0.008 inches in diameter. Alternatively, the filaments may be flat, having a thickness on the order of about 0.001–0.005 inches, and a width on the order of about 0.002–0.015 inches. By providing a relatively large number of filaments, the electrode will have sufficient strength, thereby allowing for the inclusion of smaller, and therefore more strain-resistant, filaments. In one preferred embodiment, the filaments are formed of Nitinol®. Alternatively, the electrode may include nonmetallic elements woven with metallic elements, with the nonmetallic elements providing strain resistance to support the metallic elements that provide the ablative abilities. While the ring 40 is shown in FIGS. 2 and 4 as having a smooth surface, it will be apparent that the surface may be ribbed.

Alternatively, the electrode 12 may be formed of one continuous strand of filament, which is arranged in a helical fashion around the inner member 14. The filament is expandable between a retracted position and an extended position to define an ablative ring for ablating a ring of tissue.

In one illustrative embodiment, the braided electrode 12 has a significantly greater surface area than a conventional electrode, and therefore has a relatively low impedance. Typical generators are designed to work optimally with relatively high electrode impedance values. Thus, in one embodiment of the invention, a portion of the electrode is masked so as to be non-conductive, thereby reducing the conductive surface area of the electrode and increasing the impedance level of the electrode, for optimal functioning with conventional generators.

In one embodiment, the medical device 10 includes the electrode deployment mechanism 16, which includes a proximal sheath 22 that is slidably extended over the inner member 14. The proximal sheath is connected to the proximal end of the electrode 12, and may be slidably advanced over the inner member to displace the electrode along the inner member. The electrode deployment mechanism further includes a mid sheath 24 that is slidably extended over the inner member and connected to the distal end of the electrode 12. Thus, distal advancement of the proximal sheath causes the electrode as well as the mid sheath to be driven distally over the inner member 14. A distal stop 26 is preferably mounted on the inner member 14 at a predetermined location, and is configured to engage the distal end of the mid sheath and prevent further distal displacement of the mid sheath over the inner member. The distal stop is preferably in the form of an annular ring that is extended over the inner member and which has a cross-sectional diameter that is sufficiently large to engage the distal end of the mid sheath 24 and thereby prevent further advancement of the mid sheath over the inner member 14.

In one preferred embodiment, the distal end of the mid sheath 24 is connected to the expandable stabilizing and centering device 28, which in one illustrative embodiment comprises a mesh of intertwined filaments 30 which are designed to buckle and flare radially outwardly when subjected to a compressive load, and which elongate when tensioned. The stabilizing and centering device is extended over the inner member 14 at a location distal to the electrode 12. The distal end 31 of the device 28 is preferably connected in a secure fashion to the inner member 14 at a predetermined location thereon. Thus, as the mid sheath 24 is advanced distally relative to the inner member, the filaments 30 are subjected to compression and buckle to thereby flare radially outwardly to assume an engaged position (FIG. 2) in which they engage the inner walls of a patient's lumen 32, such as an artery or vein leading to or from an atrium. By expanding radially outwardly in a uniform manner, the device 28 not only serves to anchor the medical device 10 in place relative to the patient's lumen, but also serves to center the inner member 14 within the lumen. In this manner, the electrode 12 will be properly deployed around the ostia to form a generally annular lesion, as is described in greater detail below.

Alternatively, the stabilizing and centering device 28 may be in the form of an expandable balloon 34 (FIGS. 5 and 6) which is in communication with a source of pressurized fluid (not shown) via a fluid conduit 36. The balloon is selectively expandable to extend radially outwardly from the inner member to stabilize the distal portion of the medical device 10 within the patient's lumen, and to simultaneously center the inner member 14 relative to the lumen.

In one illustrative embodiment, the medical device 10 further includes an elongated, retractable outer sheath 38 which is sized for slidable extension over the inner member 14, the deformable electrode 12, and the stabilizing and centering device 28, when the electrode and centering member are in their respective collapsed and disengaged positions. The outer sheath serves to protect the electrode 12 and device 28 during manipulation through the patient's vasculature. In addition, the outer sheath shields the electrode from the patient's tissue in the event ablation energy is prematurely delivered to the electrode.

The respective sheaths 22, 24, and 38 can be advanced and retracted over the inner member 14 in many different manners, and preferably are remotely controlled in a control handle (not shown) at the proximal end of the device 10. One suitable form of handle is disclosed in U.S. Pat. No. 5,462,527 to Stevens-Wright, the disclosure of which is hereby expressly incorporated by reference as if fully set forth herein. As described in the patent, such a handle includes a slide actuator which is axially displaceable relative to the handle. The slide actuator is preferably connected to one of the sheaths, for example, the proximal sheath 22, to control the movement of the sheath relative to the inner member 14 to drive the electrode member 12 between respective collapsed and deployed positions, as described above. The handle preferably includes a second slide actuator or other mechanism coupled to the retractable outer sheath 38 to selectively retract the sheath in a proximal direction relative to the inner member 14. Another suitable form of control handle is disclosed in U.S. Pat. No. 5,611,777 to Bowden et al., which is also expressly incorporated herein by reference.

As mentioned above, the medical device 10 of the present invention is also preferably a steerable device, and thus the control handle also preferably includes a rotatable thumb wheel rotatably mounted in the handle, which can be rotated by a user to deflect the distal end of the catheter, as is well known to those skilled in the art, and as described in greater detail in U.S. Pat. No. 5,462,527, which has been incorporated herein by reference. As is well known to those skilled in the art, the thumb wheel (or any other suitable actuating device) is engaged to one or more pull wires which extend through the inner member 14 and are connected to the distal end of the catheter at an off-axis location, whereby tension applied to one or more of the pull wires causes the distal portion of the catheter to curve in a predetermined direction or directions.

In one illustrative embodiment, the medical device 10 includes a temperature sensing device 43, such as a thermocouple, thermistor, or other suitable device, disposed at a predetermined location on the braided electrode member 12. The temperature sensing device may include a plurality of thermocouples which are weaved into the braided electrode member 12 during formation thereof, or may be one or more thermocouples or thermistors securely attached to the outer surface of the electrode member.

In operation, the medical device 10 is advanced through the patient's vasculature to the intended site of interest, for example, the ostia 11 of a vein or artery within an atrium, with the distal end of the inner member 14 extending a predetermined distance into the vein or artery so that the stabilizing and centering device 28 is disposed within the vein or artery. The clinician then retracts the protective sheath 38 to expose the electrode 12 and the stabilizing and centering device 28. Such retraction is preferably performed through a control handle as described above, but may be accomplished in any suitable manner, including grasping and manually withdrawing the sheath 38. With the electrode 12 and stabilizing and centering device 28 exposed, the clinician then manipulates the electrode deployment mechanism 16 to deploy the electrode 12 and force the device 28 into the engaged position. In one illustrative embodiment, this is performed by advancing the proximal sheath 22 in a distal direction, which forces the electrode 12 and mid sheath 24 to be advanced distally relative to the inner member 14. With the centering device 28 engaged to the inner member, distal advancement of the mid sheath causes the device 28 to be compressed so that it expands radially outwardly and into the engaged position (FIG. 2). In the engaged position, the device centers the medical device 10 relative to the patient's lumen.

As the proximal sheath 22 is further advanced over the inner member 14, the mid sheath 24 abuts against the stop 26 and is thereby prevented from being advanced further along the inner member 14. Thereafter, continued advancement of the proximal sheath results in the application of a compressive force to the filaments 20 of the electrode 12, resulting in the filaments being expanded radially outwardly from the inner member 14. Continued advancement of the proximal sheath causes the filaments to buckle and assume a generally conical, distally facing configuration (FIG. 2). In that configuration, the electrode defines the distally facing ablative ring 40 which may be brought into engagement with the patient's tissue. Ablation energy may then be delivered, for example, through the conductive inner member 14, to the electrode to ablate a continuous ring of tissue around the ostium.

While the braided electrode 12 of the device 10 is preferably manipulated to assume the forwardly facing, conical configuration, it will be apparent that the electrode may be simply manipulated to assume a disk shape, with the distally facing surface serving to ablate the ring of tissue around the ostium or other orifice. In use, the centering device 28 is situated in place within the passageway and manipulated into the expanded position. The braided electrode is then manipulated into a disk shape, with the forwardly facing surface coming into contact with the tissue around the ostium. Electrical energy is then delivered to the electrode to ablate the ring of tissue.

Referring to FIGS. 3 and 4, there is shown another embodiment of the medical device 10' according to the invention. The device 10' is identical to the device 10, except for the construction of the electrode 12'. The electrode 12' is formed in two segments, a proximal filtering segment 50 and a distal ablation segment 52. The filtering segment 50 is formed of a plurality of interwoven filaments, which may or may not be electrically conductive. The spacing between the filaments in the filtering segment is made relatively small to collect any particulate matter which flows in the blood stream during the ablation procedure.

Referring to FIG. 5, there is shown another illustrative embodiment of a medical device 100 according to the present invention. The medical device includes a radially expandable member 102 which includes a first expandable portion defining the stabilizing and centering member 34, and a second expandable portion defining an ablative electrode member 106. The expandable member is preferably an expandable balloon structure, which is selectively expandable by means of a pressurized fluid delivered through inner lumen 36. The balloon includes a reinforced central portion 108 which defines the distal member 34 and the electrode member 106. The electrode member is constructed such that when it is inflated it assumes a generally cup-shaped configuration to define a distally facing annulus 110. The electrode member also includes a flexible, ablative ring electrode 112 mounted on the annulus, such that when the balloon is expanded, the ring electrode faces distally and may be brought into contact with the ostia. Ablative energy is preferably delivered to the electrode 112 via an electrical lead 114, or any other suitable manner.

The balloon structure 102 preferably includes through passages which allow blood to pass from one side thereof to the other. Such passages may be formed in the balloon structure itself, or alternatively the inner member 14 may include an internal passageway (not shown) which allows blood to flow past the balloon structure 102.

Figure 6:
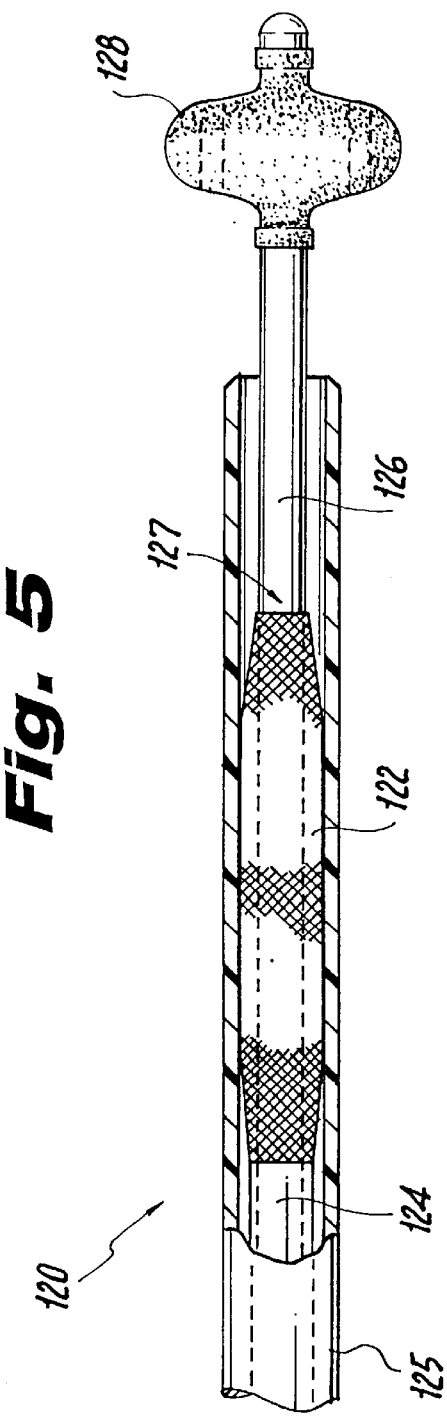
FIG. 6 is a side view of still another illustrative embodiment of a medical device according to the invention.

Referring to FIG. 6, there is shown yet another illustrative embodiment of a medical device 120 according to the invention. The device includes a braided electrode structure 122, a proximal sheath 124, and an outer sheath 125, similar to those components shown in FIG. 1. However, the distal end 127 of the electrode structure 122 is connected directly to the inner member 126. In addition, an expandable balloon device 128 is provided adjacent the distal end of the inner member to serve as the stabilizing and centering device, and is selectively expanded by pressurized fluid, as described above in connection with FIG. 5. Thus, the balloon 128 may be expanded to anchor the device 120 in place, and the proximal sheath 124 may be advanced distally over the inner member to deploy the electrode structure into the inverted configuration defining the distally facing ablative ring, as described above.

From the foregoing, it will be apparent to those skilled in the art that the present invention provides a medical device which is operative to create continuous, annular lesions. In addition, the medical device of the present invention provides an easily actuated mechanism for deploying an electrode to facilitate the creation of those continuous, annular lesions.

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A medical device for ablating a ring of tissue, the medical device comprising:
    an inner member;
    an electrically conductive member extended over the member, and including a proximal end and a distal end with a ring of ablative material defined therebetween, the electrically conductive member having a collapsed position in which the electrically conductive member extends in generally collinear fashion with the inner member and a deployed position in which the ring of ablative material is spaced radially outwardly from the inner member and is disposed distal to the distal end of the electrically conductive member; and
    an electrode deployment device slidably extended over the member and connected to the braided conductive member, the electrode deployment device being advanceable over the inner member to force the conductive member to deform and thereby define the distally facing ring.

2. The medical device of claim 1, further including an expandable stabilizing and centering structure connected to the inner member at a location distal to the braided conductive member.

3. The medical device of claim 1, further including a retractable sheath slidably extendable over the inner member and the electrically conductive member.

4. The medical device of claim 2, wherein the stabilizing and centering structure is formed of a mesh.

5. The medical device of claim 2, wherein the stabilizing and centering structure comprises an expandable balloon.

6. A medical device for ablating a ring of tissue, the medical device comprising:
    an inner member;
    a braided, electrically conductive member extended over the inner member, and including a proximal end and a distal end, the electrically conductive member being deformable to define a distally facing ring of ablative material; and
    an electrode deployment device slidably extended over the inner member and connected to the braided conductive member, the electrode deployment device being advanceable over the inner member to force the conductive member to deform and thereby define the distally facing ring,
    wherein the braided, electrically conductive member comprises a filter portion and an electrically conductive portion, with the filter portion being connected to the electrode deployment device.

7. The medical device of claim 1, wherein the inner member is electrically conductive and is connected to the electrically conductive member to deliver electrical energy thereto.

8. The medical device of claim 1, wherein a selected portion of the braided, electrically conductive member is masked to be non-conductive.

9. The medical device of claim 1, further including a temperature sensing device connected to the electrically conductive member.

10. A medical device for ablating a ring of tissue, the medical device comprising:
    an elongated inner member;
    an electrically conductive member extended over the inner member and including a proximal end and a distal end with a ring of ablative material defined therebetween, the electrically conductive member having a collapsed position in which the electrically conductive member extends in generally collinear fashion with the inner member and a deployed position in which the ring of ablative material is spaced radially outwardly from the inner member and is disposed distal to the distal end of the electrically conductive member; and
    means for deforming the electrically conductive member into the deployed position.

11. The medical device of claim 10, wherein the means for deforming comprises a proximal sheath slidably extended over the inner member and connected to the braided, electrically conductive member, and a stop disposed distally of the proximal sheath, such that with the proximal sheath advanced distally, the sheath and stop cooperate to deform the braided, electrically conductive member.

12. The medical device of claim 10, further including an expandable stabilizing and centering structure connected to the inner tubular member at a location distal to the electrically conductive member.

13. The medical device of claim 10, further including a retractable sheath slidably extendable over the inner member and the electrically conductive member.

14. The medical device of claim 10, wherein the stabilizing and centering structure is formed of a mesh.

15. The medical device of claim 10, wherein the stabilizing and centering structure comprises an expandable balloon.

16. A medical device for ablating a ring of tissue, the medical device comprising:
    an elongated inner member;
    a braided, electrically conductive member extended over the inner member; and
    means for deforming the braided, electrically conductive member to define a distally facing ring of ablative material,
    wherein the braided, electrically conductive member comprises a filter portion and an electrically conductive portion, with the filter portion being connected to the proximal sheath.

17. The medical device of claim 10, wherein the inner member is electrically conductive and is connected to the electrically conductive member to deliver electrical energy thereto.

18. The medical device of claim 10, wherein a selected portion of the electrically conductive member is masked to be non-conductive.

19. The medical device of claim 12, wherein a selected portion of the electrically conductive member is masked to be non-conductive.

20. A medical device for ablating a ring of tissue, the medical device comprising:
    an elongated inner member;
    an expandable stabilizing and centering member mounted on the inner member, the centering member being expandable to anchor at least a portion of the inner member within a passageway; and
    means on the inner member for creating a generally annular lesion, said means comprising an electrically conductive member extended over the inner member and including a proximal end and a distal end with a ring of ablative material defined therebetween, the electrically conductive member having a collapsed position in which the electrically conductive member extends in generally collinear fashion with the inner member and a deployed position in which the ring of ablative material is spaced radially outwardly from the inner member and is disposed distal to the distal end of the electrically conductive member.

21. The medical device of claim 20, wherein the means for creating comprises an expandable, electrically conductive member extended over the inner member.

22. The medical device of claim 20, wherein the means for creating comprises an expandable balloon connected to the inner member, the balloon including an ablative member which assumes a generally annular, distally facing configuration when the balloon is inflated.

23. The medical device of claim 21, further including a retractable sheath slidably extendable over the inner member and the electrically conductive member.

24. The medical device of claim 20, wherein the stabilizing and centering member is formed of a mesh.

25. The medical device of claim 20, wherein the stabilizing and centering structure comprises an expandable balloon.

26. A medical device for ablating a ring of tissue, the medical device comprising:
    an elongated inner member;
    an expandable stabilizing and centering member mounted on the inner member, the centering member being expandable to anchor at least a portion of the inner member within a passageway; and
    an expandable, braided, electrically conductive member extended over the inner member which is adapted to create a generally annular lesion,
    wherein the braided, electrically conductive member comprises a filter portion and an electrically conductive portion, with the filter portion being connected to the proximal sheath.

27. The medical device of claim 21, wherein the inner member is electrically conductive and is connected to the electrically conductive member to deliver electrical energy thereto.

28. The medical device of claim 21, wherein a selected portion of the electrically conductive member is masked to be non-conductive.

29. The medical device of claim 27, wherein a selected portion of the electrically conductive member is masked to be non-conductive.

30. A medical device for ablating a ring of tissue, the medical device comprising:
    an inner member;
    a braided, electrically conductive member slidably extended over the member, the electrically conductive member being deformable to assume a generally conical configuration and define a distally facing, ablative ring;
    a proximal sheath slidably extended over the member and connected to a proximal end of the braided, conductive member;
    a second sheath slidably extended over the member and connected to a distal end of the braided, conductive member;
    a stop formed on the inner member at a location distal of the second sheath to prevent movement of the second sheath past the stop;
    wherein the proximal sheath is advanceable distally over the inner member to force the second sheath against the stop and to cause the conductive member to deform and assume the generally conical configuration and define the distally facing ablative ring.

31. The medical device of claim 30, further including an expandable stabilizing and centering structure connected to the inner member at a location distal to the braided conductive member.

32. The medical device of claim 30, further including a retractable sheath slidably extendable over the inner member and the braided, electrically conductive member.

33. The medical device of claim 31, wherein a distal end of the centering structure is connected to the inner member, and a proximal end thereof is connected to the second sheath.

34. The medical device of claim 31, wherein the stabilizing and centering structure is formed of a mesh.

35. The medical device of claim 31, wherein the stabilizing and centering structure comprises an expandable balloon.

36. The medical device of claim 30, wherein the braided, electrically conductive member comprises a filter portion and an electrically conductive portion, with the filter portion being connected to the proximal sheath.

37. The medical device of claim 30, wherein the inner member is electrically conductive and is connected to the braided, electrically conductive member to deliver electrical energy thereto.

38. The medical device of claim 30, wherein a selected portion of the braided, electrically conductive member is masked to be non-conductive.

39. The medical device of claim 30, wherein a selected portion of the braided, electrically conductive member is masked to be non-conductive.

40. The medical device of claim 30, wherein the electrically conductive member has a collapsed position in which the electrically conductive member extends in generally collinear fashion with the inner member and a deployed position in which the ring of ablative material is spaced radially outwardly from the inner member and is disposed distal to the distal end of the electrically conductive member.

* * * * *